(12) United States Patent
Papastathopoulos et al.

(10) Patent No.: US 11,033,432 B2
(45) Date of Patent: Jun. 15, 2021

(54) PRODUCING CUT SURFACES IN A TRANSPARENT MATERIAL BY MEANS OF OPTICAL RADIATION

(71) Applicant: Carl Zeiss Meditec AG, Jena (DE)

(72) Inventors: Evangelos Papastathopoulos, Ludwigsburg (DE); Gregor Stobrawa, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 86 days.

(21) Appl. No.: 16/144,326

(22) Filed: Sep. 27, 2018

(65) Prior Publication Data

US 2019/0021905 A1 Jan. 24, 2019

Related U.S. Application Data

(63) Continuation of application No. 14/353,265, filed as application No. PCT/EP2012/070896 on Oct. 22, 2012, now Pat. No. 10,105,262.

(30) Foreign Application Priority Data

Oct. 21, 2011 (DE) .......................... 102011085046.5

(51) Int. Cl.
*A61F 9/008* (2006.01)
(52) U.S. Cl.
CPC ........ *A61F 9/0084* (2013.01); *A61F 9/00825* (2013.01); *A61F 2009/0087* (2013.01);
(Continued)
(58) Field of Classification Search
USPC ....................................................... 606/4–6
See application file for complete search history.

(56) References Cited

U.S. PATENT DOCUMENTS 4,901,718 A 2/1990 Bille et al.
5,336,215 A 8/1994 Hsueh et al.
(Continued)

FOREIGN PATENT DOCUMENTS

CN 1154658 A 7/1997
CN 10168687 A 3/2010
(Continued)

OTHER PUBLICATIONS

Lubatschowski, Holger, et al., "Medical applications for ultrafast laser Pulses," RIXEN Review No. 50, pp. 113-118 (Jan. 2003).

*Primary Examiner* — Lynsey C Eiseman
(74) *Attorney, Agent, or Firm* — Christensen, Fonder, Dardi & Herbert PLLC

(57) ABSTRACT

A method for producing a cut surface in a transparent material using optical radiation. A laser device separates the material using optical radiation and includes an optical unit focusing the radiation along an optical axis into an image field defining an image-field size. A focal position is adjusted transversely along the axis, producing a cut surface extending substantially parallel to the axis and, in projection along the axis, is a curve having a maximum extent. The focus is displaced by adjustment of the focal position along a trajectory curve lying in the cut surface. The cut surface has a maximum extent which is greater than the image-field size. The focal position is moved transverse to the axis along the curve. The image field is displaced transversely, and the focal position is adjusted in an oscillating fashion along the axis on the curve between an upper and lower axial focus position.

21 Claims, 6 Drawing Sheets

(52) U.S. Cl.
CPC ............... *A61F 2009/00889* (2013.01); *A61F 2009/00897* (2013.01)

(56) References Cited

U.S. PATENT DOCUMENTS

| | | |
|---|---|---|
| 5,520,679 A | 5/1996 | Lin |
| 5,549,632 A | 8/1996 | Lai |
| 5,618,285 A | 4/1997 | Zair |
| 5,656,186 A | 8/1997 | Mourou et al. |
| 5,984,916 A | 11/1999 | Lai |
| 5,993,438 A | 11/1999 | Juhasz et al. |
| 6,110,166 A | 8/2000 | Juhasz |
| 6,254,595 B1 | 7/2001 | Juhasz et al. |
| 6,325,792 B1 | 12/2001 | Swinger et al. |
| 6,497,701 B2 | 12/2002 | Shimmick et al. |
| 6,590,670 B1 | 7/2003 | Kato et al. |
| 6,607,527 B1 | 8/2003 | Ruiz et al. |
| 6,608,674 B2 | 8/2003 | Gerlach et al. |
| 7,101,364 B2 | 9/2006 | Bille |
| 7,486,409 B2 | 2/2009 | Yamashita et al. |
| 7,621,637 B2 | 11/2009 | Rathjen |
| 2001/0031960 A1 | 10/2001 | Kliewer et al. |
| 2002/0035359 A1 | 3/2002 | Yee et al. |
| 2002/0173779 A1 | 11/2002 | Donitzky |
| 2003/0014042 A1 | 1/2003 | Juhasz et al. |
| 2003/0105457 A1 | 6/2003 | Mrochen et al. |
| 2004/0070761 A1 | 4/2004 | Horvath et al. |
| 2004/0199150 A1 | 10/2004 | Lai |
| 2004/0254568 A1 | 12/2004 | Rathjen |
| 2005/0107773 A1 | 5/2005 | Bergt et al. |
| 2007/0073279 A1 | 3/2007 | Rowe et al. |
| 2007/0179483 A1 | 8/2007 | Muhlhoff et al. |
| 2008/0033406 A1* | 2/2008 | Andersen ............... A61F 9/008 606/4 |
| 2008/0077121 A1 | 3/2008 | Rathjen |
| 2008/0177256 A1 | 7/2008 | Loesel et al. |
| 2008/0192783 A1* | 8/2008 | Rathjen ............... A61F 9/0084 372/25 |
| 2009/0005764 A1 | 1/2009 | Knox et al. |
| 2009/0171329 A1 | 7/2009 | Raksi et al. |
| 2011/0022036 A1 | 1/2011 | Frey et al. |
| 2011/0028951 A1 | 2/2011 | Raksi et al. |
| 2011/0028955 A1 | 2/2011 | Raksi |
| 2011/0028958 A1 | 2/2011 | Raksi et al. |
| 2011/0034911 A1 | 2/2011 | Bischoff et al. |
| 2011/0071509 A1 | 3/2011 | Knox et al. |
| 2011/0224658 A1 | 9/2011 | Bischoff et al. |
| 2011/0245816 A1 | 10/2011 | Abe |
| 2011/0251601 A1 | 10/2011 | Bissmann et al. |
| 2011/0264081 A1 | 10/2011 | Reich et al. |
| 2012/0016352 A1 | 1/2012 | Dick et al. |
| 2013/0197634 A1 | 8/2013 | Palanker et al. |

FOREIGN PATENT DOCUMENTS

| | | |
|---|---|---|
| DE | 695 00 997 T2 | 4/1998 |
| DE | 100 34 251 C1 | 9/2001 |
| DE | 101 24 358 C1 | 10/2002 |
| DE | 103 23 422 A1 | 4/2004 |
| DE | 103 34 108 A1 | 2/2005 |
| DE | 10 2008 017 293 A1 | 10/2009 |
| DE | 10 2008 027 358 A1 | 12/2009 |
| DE | 10 2008 056 488 A1 | 5/2010 |
| DE | 10 2008 062 658 A1 | 6/2010 |
| DE | 10 2009 012 873 A1 | 9/2010 |
| EP | 1 159 986 A2 | 12/2001 |
| EP | 1 486 185 A1 | 12/2004 |
| EP | 2 371 328 A1 | 10/2011 |
| JP | 11-192253 A | 7/1991 |
| JP | 6-277248 A | 10/1994 |
| JP | 2000-116694 A | 4/2000 |
| WO | WO 93/16631 A1 | 9/1993 |
| WO | WO 94/09849 A1 | 5/1994 |
| WO | WO 97/30752 A1 | 8/1997 |
| WO | WO 98/14244 A1 | 4/1998 |
| WO | WO 01/85075 A1 | 11/2001 |
| WO | WO 02/32353 A2 | 4/2002 |
| WO | WO 03/059563 A2 | 7/2003 |
| WO | WO 2004/032810 A1 | 4/2004 |
| WO | WO 2006/074469 A2 | 7/2006 |
| WO | WO 2009/003107 A1 | 12/2008 |
| WO | WO 2010/051975 A1 | 5/2010 |
| WO | WO 2010/070020 A2 | 6/2010 |
| WO | WO 2011/017002 A2 | 2/2011 |
| WO | WO 2011/017004 A2 | 2/2011 |
| WO | WO 2011/061160 A1 | 5/2011 |
| WO | WO 01/67978 A1 | 9/2011 |

* cited by examiner

PRODUCING CUT SURFACES IN A TRANSPARENT MATERIAL BY MEANS OF OPTICAL RADIATION

PRIORITY CLAIM

The present application is a Continuation Application of U.S. patent application Ser. No. 14/353,265, filed Apr. 21, 2014 which is a National Phase entry of PCT Application No. PCT/EP2012/070896, filed Oct. 22, 2012, which claims priority from German Application Number 102011085046.5, filed Oct. 21, 2011, the disclosures of which are hereby incorporated by reference herein in their entirety.

FIELD OF THE INVENTION

The invention relates to a method for producing a cut in a transparent material by means of optical radiation, wherein a laser device is used which is adapted to generate a cut within the transparent material by means of the optical radiation and which comprises optics which focus the optical radiation along an optical axis into a focus situated in the material and which have in the material an image field in which the focus lies and which has an image field size, wherein a position of the focus is moved transverse to the optical axis and along the optical axis, wherein the cut extends parallel to the optical axis and is a curve in projection along the optical axis and has a maximum extent in projection along the optical axis, and wherein the focus is shifted by the movement of the position of the focus along a path lying in the cut.

The invention further relates to a method for producing control data for producing a cut in a transparent material, wherein the control data are adapted for a laser device which is adapted to generate the cut within the transparent material by means of optical radiation and which comprises optics which focus the optical radiation along an optical axis into a focus situated in the material and which have in the material an image field in which the focus lies and which has an image field size, wherein the laser device further comprises a focus adjustment device for moving a position of the focus transverse to the optical axis and along the optical axis, wherein the control data predetermine a path along which the position of the focus of the optical radiation is to be moved in the material to produce the cut in such a way that the cut extends parallel to the optical axis, is a curve in a projection along the optical axis and has a maximum extent in a projection along the optical axis.

The invention further relates to a treatment apparatus for producing a cut in a transparent material, which comprises a laser device which is adapted to generate a cut within the transparent material by means of optical radiation and which has optics which focus the optical radiation along an optical axis into a focus situated in the material and which have in the material an image field in which the focus lies and which has an image field size, wherein the apparatus further comprises a focus adjustment device for moving a position of the focus transverse to the optical axis and along the optical axis, a control device which is connected to the laser device and controls the laser device such that the focus adjustment device moves the position of the focus of the optical radiation in the material along a path, wherein the control device controls the laser device such that the cut extends parallel to the optical axis, is a curve in projection along the optical axis and has a maximum extent in projection along the optical axis.

This method and device are used in particular in the field of ophthalmology.

BACKGROUND OF THE INVENTION

In the field of ophthalmology, as well as in other applications, optical radiation acts inside the material, for example, the tissue, which is transparent to the optical radiation. Non-linear processes are usually used which require a focusing of machining radiation, usually pulsed laser radiation, into the material, i.e., underneath the surface of the material. The production of a cut occurs by displacing the position of the focus in the material. With the knowledge that forms the basis of this description, the shift of the focus does not necessarily require that radiation is also emitted into the focus at this time. In particular when pulsed laser radiation is used, the focus is continuously shifted and laser radiation pulses are only emitted at certain times during the focus shift. Nevertheless the corresponding optics and the focus adjustment device operate continuously, which is why the term "focus shift" herein is also understood to mean the corresponding shift of the point at which optical radiation would be focused, even if such radiation is momentarily not emitted, e.g., between two laser pulses.

The high focusing of the laser radiation, i.e., a geometrically strongly delimited focus, is of great importance for non-linear effects, as only then can the necessary power densities in the material be achieved. This applies both to non-linear processes in which an individual focus already results in an interaction and to processes in which several laser radiation pulses which are emitted one after the other interact to achieve a material-cutting effect. In this regard, approaches are also known in which laser radiation pulses are emitted at several overlapping focus spots and only the interaction of the several laser radiation pulses leads to material cutting in the overlap area.

Three-dimensional cuts, which extend parallel to the optical axis of the radiation incidence (of the so-called main direction of incidence), are e.g., required as cylindrical-jacket-shaped cuts in the field of ophthalmology, in particular in cataract surgery. Here a circular opening with a particular diameter is produced in the front of the capsular bag. The shape of the cut is then a circular cylinder, which is oriented approximately parallel to the optical axis and thus also parallel to the main direction of incidence of the optical radiation.

EP 1486185 relates to an apparatus for cataract surgery in which the laser radiation is conveyed to the handle with the aid of an optical fiber. A collimator is mechanically adjusted in the handle in order to adjust the position of the focus along the optical axis. The focus can therefore be adjusted along the optical axis only very slowly as rapid movement of the collimator would result in undesired vibrations and thermal loading of the handle. Moreover, the use of an optical fiber at the powers required for eye surgery is extremely problematic.

A method is described in U.S. Pat. Nos. 7,486,409 and 6,590,670 for rapidly varying the depth position of a focus on the basis of a vibrating tuning fork. At least one lens of an optical arrangement is fixed to the vibrating arm of a tuning fork which is made to vibrate by an electromagnet. For adjusting the depth, DE 10034251 proposes attaching a corner reflector to the vibrating arm of a tuning fork. The corner reflector is illuminated with a non-collimated light beam and the propagation of the light beam which is reflected back is varied by adjusting the position of the corner reflector. If the light beam is focused using an objective lens, a rapid variation of the focus position in the depth direction, i.e., along the optical axis, is obtained. These tuning fork arrangements were proposed for optical measurement technology.

For producing three-dimensional cuts which extend parallel to the optical axis of the radiation incidence, laser treatment apparatuses are known which have an optical unit and device for three-dimensional focus adjustment. Such treatment apparatuses shift the focus in the image field and supplement this two-dimensional shift with a shift of the image field plane to obtain a three-dimensional focus position setting. Since the shift of the image field plane is much slower than the two-dimensional shift of the focus position in the image plane, care must be taken with such apparatuses that the image plane shift is needed as little as possible, in order to design the production of cuts to be as rapid as possible. Therefore, for example, spiral-shaped trajectories are known from the state of the art, which combine rapid shift in the image plane with a comparatively slow shift or adjustment of the image plane position. In this way, for example, cylindrical cuts, which lie parallel to the optical axis, can be produced very quickly.

A disadvantage of this approach is that the optics must be designed such that a rapid two-dimensional shift of the focus position is possible in the image field. The image field size must also be designed such that desired cut sizes are covered.

SUMMARY OF THE INVENTION

An object of the invention is therefore to develop methods and machining devices such that cuts in particular cylindrical-jacket-shaped cuts which run substantially parallel to the optical axis and can be produced with little outlay.

The object is achieved according to an embodiment of the invention by a method for producing a cut in a transparent material by means of optical radiation, wherein a laser device is used which is adapted to generate a cut within the transparent material by means of the optical radiation and which comprises optics which focus the optical radiation along an optical axis into a focus situated in the material and which have in the material an image field in which the focus lies and which has an image field size, wherein a position of the focus is moved transverse to the optical axis and along the optical axis, as a result of which the cut is produced, which extends parallel to the optical axis and is, in projection along the optical axis, a curve which has a maximum extent, and wherein the focus is shifted by moving the position of the focus along a path, which lies in the cut, wherein, transverse to the optical axis, the cut has a maximum extent which is greater than the image field size. In order to shift the focus along the path, the position of the focus is moved transverse to the optical axis along the curve, wherein the image field is shifted transverse to the optical axis and the position of the focus along the optical axis is moved several times in an oscillating manner between an upper axial focus position and a lower axial focus position during the movement along the curve.

The object is likewise achieved by a method for producing control data for producing a cut in a transparent material, wherein the control data are adapted for a laser device which is adapted to generate a cut within the transparent material by means of optical radiation and which comprises optics which focus the optical radiation along an optical axis into a focus situated in the material and which have in the material an image field in which the focus lies and which has an image field size, wherein the laser device further comprises a focus adjustment device for moving a position of the focus transverse to the optical axis and along the optical axis. The control data predetermine a path along which the position of the focus of the optical radiation is to be moved in the material to produce the cut in such a way that the cut extends parallel to the optical axis and is, in projection along the optical axis, a curve which has a maximum extent, wherein the control data predetermine the path such that, transverse to the optical axis, the cut has a maximum extent which is greater than the image field size, the control data define for the focus adjustment device a movement of the position of the focus along the curve, wherein a shift of the image field transverse to the optical axis is defined and wherein the control data define for the focus adjustment device a multi-oscillating movement of the position of the focus along the optical axis between an upper axial focus position and a lower axial focus position during the movement along the path.

The object is also achieved by a treatment apparatus for producing a cut in a transparent material, the apparatus comprising a laser device that is adapted to generate a cut within the transparent material by means of optical radiation and that has optics which focus the optical radiation along an optical axis into a focus situated in the material and which has in the material an image field in which the focus lies and which has an image field size, wherein the apparatus further comprises a focus adjustment device for moving a position of the focus transverse to the optical axis and along the optical axis, a control device which is connected to the laser device and controls the laser device such that the focus adjustment device moves the position of the focus of the optical radiation in the material along a path, wherein the control device controls the laser device such that the cut extends parallel to the optical axis and defines, in projection along the optical axis, a curve which has a maximum extent, wherein the focus adjustment device shifts the image field transverse to the optical axis to move the focus transverse to the optical axis and the control device controls the laser device such that, transverse to the optical axis, the cut has a maximum extent which is greater than the image field size, and defines for the focus adjustment device a movement of the position of the focus transverse to the optical axis in the form of a movement of the position of the focus along the curve and, defines a multi-oscillating movement of the position of the focus between an upper axial focus position and a lower axial focus position during the movement along the curve.

An embodiment of the invention uses a path to produce the cut, the path differing fundamentally from the usual approach which aims to minimize an axial shift of the focus as much as possible. Rather, the position of the focus is now adjusted much more slowly transverse to the optical axis (so-called lateral adjustment) than axial, by guiding the focus position on the curve which the cut has in projection along the optical axis. This curve is the elevation line of the cut. It is preferably a closed curve, e.g., a periodic Lissajous figure, for example, a circle, an ellipse etc. The focus is shifted in an oscillating manner perpendicular thereto, i.e., axially, or along the optical axis. A path is thus obtained which, in a side view of the cut seen perpendicular to the optical axis, moves back and forth in a meandering shape between the lower and the upper edge of the cut corresponding to the lower and the upper axial focus position.

The cut which is produced by the method, for which the control data are designed and which sets the control apparatus of the machining device defines and sets, extends, as already mentioned, optionally only substantially and not necessarily strictly, parallel to the optical axis. Deviations from the parallel which are small compared to the length of the curve are acceptable. In particular in laser devices which have a small image field compared with the extent of the zone to be treated and which work with an image field shift, it is possible to carry out an additional focus shift within this small image field. This allows, of course, to additionally deflect the position of the focus laterally while the image field is being moved along the curve. The cut can thereby have areas in which there is no strict parallelism to the optical axis. Equally it is possible to produce a cut which is inclined in relation to the optical axis at least in sections by controlling the additional focus shift within the image field such that as a whole the cut is slightly at an angle. In this case, the additional lateral focus shift within the image field is suitably synchronized with the oscillating axial focus shift.

The movement of the focus does not necessarily require that optical radiation be emitted onto every focus position for material to be cut. It is thus much simpler, for example, when using pulsed radiation, to continuously shift the focus, with the result that the spots onto which laser radiation pulses are emitted are spaced apart in the material corresponding to the path speed of the focus. If an optical break-through which produces a plasma bubble is utilized for the material-cutting effect, it is even preferred to maintain a certain distance between the spots onto which the individual laser radiation pulses are emitted. Methods are also known, however, in which several laser radiation pulses cooperate to cut material without producing an optical break-through. These approaches are also called subthreshold methods.

Furthermore, the shift of the focus along the path described does not rule out that no laser radiation of a material-cutting effect is emitted to individual sections of the path along which the focus is guided. In particular, when using material cutting based on plasma bubbles, sections of the path are relevant here on which the focus is moved from top to bottom, i.e., in the direction of incidence of the optical radiation. If plasma bubbles are produced for the material cutting, no further optical break-through and plasma bubbles can be produced in zones below a recently formed plasma bubble (which can be much bigger than the focus) at least for some period as each plasma bubble lying above interferes with the focus quality in such a way that an optical break-through can no longer be definitely achieved. Within the scope of the invention it is therefore entirely possible to blank the optical radiation, i.e., to switch it off or at least to deactivate with respect to its material-machining effect, in those sections of the path in which the focus moves down, i.e., away from the laser device. Various approaches are known in the state of the art for such deactivations, for example, laser-pulse lengthening, focus degradation, spectral changes, changes in polarization, etc. Within the scope of the invention, a method is therefore advantageous in which, on sections of the path in which the position of the focus moves with (i.e., in the same direction as) a direction of incidence of the optical radiation, the optical radiation is switched off or modified such that the optical radiation has no material-cutting effect in the transparent material.

In order also in such cases to cover the cuts as closely as possible with sections of the path in which the optical radiation has a material-cutting effect, it is preferred to design the oscillation to be asymmetrical, with the result that sections of the path in which the position of the focus moves with the direction of incidence of the optical radiation run more steeply than sections of the path in which the position of the focus moves contrary to the direction of incidence of the optical radiation.

The cut can be bi-connected in the mathematical sense. The curve is then closed. The cut produced can, in particular, be in the shape of a cylindrical surface, which is advantageous in applications to the mentioned cataract surgery. Equally, the cut can, of course, also be used to section or change transparent material, for example, eye tissue. Among other things, sectioning the crystalline lens before removal in cataract surgery or the targeted weakening of the cornea with the aim of thereby modifying the curvature of the cornea to correct defective vision comes into consideration. In particular, but not exclusively for these applications, closed, i.e., periodic, Lissajous figures which cross each other are suitable. Such Lissajous figures can be achieved by carrying out a biaxial deflection according to harmonic functions which are based on integer multiples of a basic function, wherein the integer multiples are different for the two deflection axes.

The cut can, however, also be simply connected; the curve is then a non-closed line.

If a material cutting is carried out at the axially upper or lower focus position, these focus positions automatically define the upper or lower edge of the cut respectively.

The shift of the image field makes it possible to dispense with expensive optical units having an image field large enough to cover the entire treatment zone. However, it may also be pointed out that it is entirely possible to modify the treatment apparatus or the method such that the lateral shift of the position of the focus is done without a shift of the image field if the image field size is greater than the maximum size of the envisaged, sought or produced cut. Such an extension lies within the scope of the invention. The advantage is then retained that the shift of the focus can be carried out much more slowly transversely to the optical axis than along the optical axis. For applications in ophthalmology, the image field in the eye should then at least have a diameter of approximately 5 mm.

If smaller image fields are used and it is nevertheless desired to produce structures which have a maximum lateral extent transversely which is greater than the image field size, the image field can be shifted particularly easily by moving the optics or an optical element transverse to the optical axis. This can be done in combination with a lateral focus shift within the image field.

The device and the method for producing a cut are particularly advantageously applicable in cataract surgery. A movable handpiece, which is placed on the eye, is required for such surgery. It is therefore preferred that the laser device has a base part and a movable handpiece, which are connected to each other via a flexible or articulated transmission device, wherein the focus adjustment device is formed by two parts and has a first scanner, which adjusts the position of the focus along the optical axis and is arranged in the base part, and a second scanner, which adjusts the position of the focus transversely with respect to the optical axis and of which at least one component is arranged in the handpiece. In the second scanner for adjusting the position of the focus transversely with respect to the optical axis, this component is preferably an actuator for displacing an objective lens transversely with respect to the optical axis.

The transmission device can preferably comprise bulk optics. It has proved to be advantageous if the base part couples a non-collimated light bundle into the transmission device, thus a light bundle which has a particular divergence or convergence state. The transmission device, for example, a corresponding articulated arm, guides this light bundle from the base part to the handle while maintaining divergence or convergence state. The transverse displacement of the objective lens to realize the xy-scanning procedure is then combined with a corresponding activation of a divergence-modifying device, which influences the divergence or convergence of the non-collimated beam, in order to compensate for a change in the path length which arises as a result of the transverse displacement of the objective lens. This prevents the transverse displacement of the objective lens, i.e., the image field adjustment for the xy-scanning, from bringing with it, in an undesired manner, a shift of the focus position along the optical axis.

The divergence-modifying device can particularly preferably be arranged in the base part as the handle then remains compact. It can be realized as a telescope with an actuator that adjusts it.

The use of a non-collimated beam path between base part and handle further has the advantage that the z-scanner can be realized particularly easily by the first scanner adjusting the path length of the non-collimated beam path. A retroreflector, for example, a corner mirror, can be used for this path length adjustment. The use of the non-collimated beam path makes it possible to adjust the depth position of the focus easily by changing the path length of the beam path to the objective lens. However, there must be a non-parallel beam path between the first scanner and the objective lens since a parallel beam path would undo the effect of the first scanner. The beam path from the z-scanner to the objective lens is consequently not telecentric.

In an embodiment, the base part comprises a non-collimated, i.e., diverging or converging beam path section and the first scanner comprises a corner mirror, which lies in this beam path section. To shift the position of the focus along the optical axis, the corner mirror is displaced in order to change the length of the non-collimated beam path section.

The corner mirror can be displaced particularly quickly by an oscillator, which makes the corner mirror vibrate to periodically change the length of the non-collimated beam path section. Alternatively, it is possible to mount several corner mirrors on a rotating disc, which pass through the non-collimated beam path section one after the other.

It is understood that the features mentioned above and those yet to be explained below can be used, not only in the stated combinations, but also in other combinations or singly, without departing from the scope of the present invention. The description of method features for material cutting or for producing control data also relates equally to a corresponding embodiment of the control device, which controls the treatment apparatus. Conversely, features which are described in relation to the treatment apparatus, in particular its control device, are equally relevant to the corresponding method for material treatment or for producing control data.

The production of control data can be carried out separately from, i.e., independently of, the treatment apparatus. Of course, it presupposes corresponding knowledge about the treatment apparatus for which the control data are provided.

BRIEF DESCRIPTION OF THE DRAWINGS

The invention is explained in further detail below by way of example with reference to the attached drawings which also disclose features of the invention wherein.

DETAILED DESCRIPTION

Figure 1:
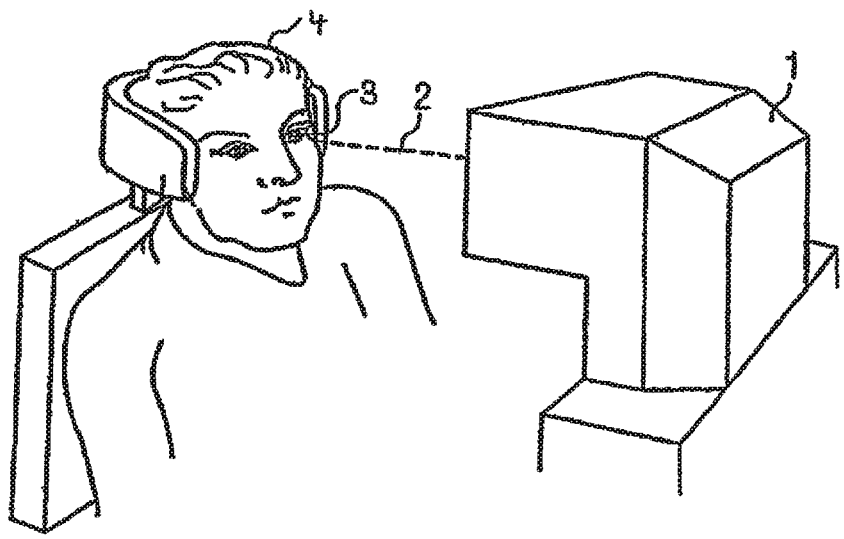
FIG. 1 depicts a schematic representation of an embodiment of a treatment apparatus for ophthalmological surgery, in particular for correcting defective vision.

FIG. 1 shows a treatment apparatus 1 for eye surgery. For example, an eye-surgery process which is similar to that described in EP 1 159 986 A2 and U.S. Pat. No. 5,549,632 can be carried out with it. The treatment apparatus 1 produces a material cutting in transparent material by means of treatment laser radiation 2. This material cutting can be e.g., a production of cuts, in particular the treatment apparatus for correcting defective vision can generate a change on an eye 3 of a patient 4. The defective vision can include hyperopia, myopia, presbyopia, astigmatism, mixed astigmatism (astigmatism in which there is hyperopia in one direction and myopia in a direction at right angles thereto), aspheric errors and higher-order aberrations. The material cutting can be used in the field of corneal surgery but also on other tissues of the eye, e.g., in cataract surgery. While reference is made to eye surgery below, this is to be understood in each case only by way of example and not as limiting.

In the embodiments described, the components of the apparatus 1 are controlled by an integrated control unit, which, however, can of course also be provided as a stand-alone unit.

Figure 2:
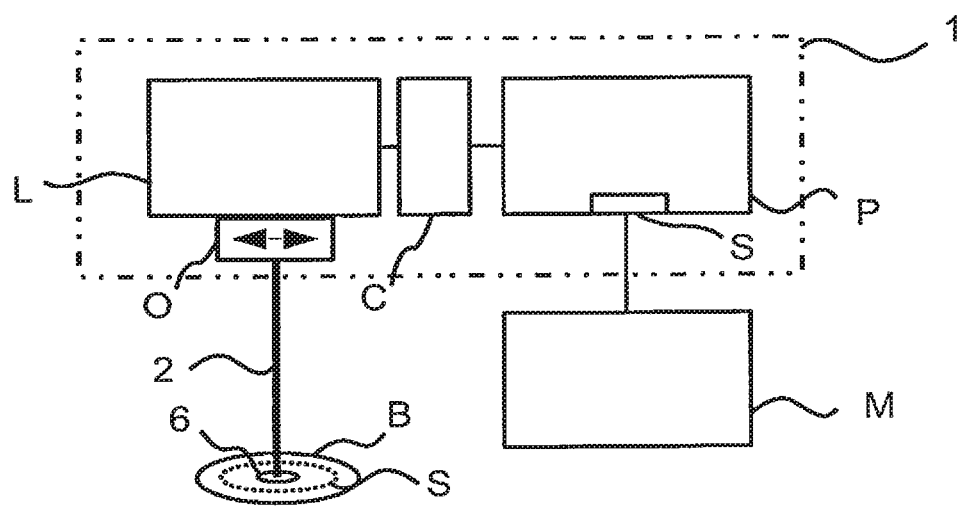
FIG. 2 depicts a schematic representation with regard to the structure of the treatment apparatus of FIG. 1.

FIG. 2 shows the treatment apparatus 1 schematically. In this variant it has at least three devices or modules. Laser device L emits the laser beam 2 onto the material, e.g., an eye, via optics O and moves the position of the focus in the material in three spatial directions. The shift along the main direction of incidence of the optical radiation (z-axis) is called axial shift and the shift perpendicular thereto is called lateral shift. In the variant shown in FIG. 2, the optics O has an image field B, in which a focus 6 of the laser radiation 2 lies, which image field is smaller than the extent of the zone to be treated. In order to shift the position of the focus 6 in the material lateral, the objective lens of the laser device L is displaced transverse to the optical axis. This is indicated in FIG. 2 by a double arrow for the objective lens. The focus 6 together with the image field B is thereby displaced. Optionally, the focus 6 can additionally be fine shifted in an area S within the image field B.

In an alternative variant, the laser device L has lateral scanning device, which shifts the focus 6 in the image field B, which is large enough to cover the extent of the zone to be treated. An axial scanning device is additionally provided.

In all variants, the operation of the laser device L is fully automatic, controlled by integrated or separate control device C. In response to a corresponding start signal the laser device L starts to move the laser beam 2 and thereby produces cuts in a manner yet to be described.

The control device C operates according to control data which either have been produced by it or have been supplied to it. In the latter case, which is shown in FIG. 2, the control data necessary for operation are supplied to the control device C beforehand as a control data set by planning device P via control lines not identified in more detail. The determination or transmission of the control data takes place prior to operation of the laser device L. Of course, the communication can also be wireless. As an alternative to direct communication, it is also possible to arrange the planning unit P physically separated from the laser unit L, and to provide a corresponding data transmission channel.

In ophthalmology, the defective vision of the eye 3 is preferably measured with one or more measuring devices M before the treatment apparatus 1 is used. The measured values are then supplied to the control device or the planning device P and form the basis for the production of control data. In particular, the position and/or extent of an area to be treated, in particular to be sectioned, can be measured.

The control device or the planning device P produces the control data set from the measurement data which have been determined, e.g., for the eye to be treated. They are supplied to the planning device P via an interface S and, in the embodiment shown, come from measuring device M which has previously taken measurements of the eye of the patient 4. Of course, the measuring device M can transfer the corresponding measurement data to the planning device P or directly to the control device C in any desired manner.

In the embodiment described, the laser radiation 2 is focused as a pulsed laser beam into the material, e.g., the eye 3. The pulse duration produced by the laser device L in this case is e.g., in the femtosecond range, and the laser radiation 2 acts through non-linear optical effects in the material, e.g., the capsular bag, the crystalline lens or the cornea. The laser beam has laser pulses as short as e.g., 50 to 800 fs (preferably 100-400 fs) with a pulse repetition frequency of between 10 kHz and 10 MHz. The type of material-cutting effect which the treatment apparatus 1 utilizes with the laser radiation 2, however, is of no further relevance for the following description, in particular there is no necessity to use pulsed laser radiation, though a focus of treatment radiation 2 in the material should be shifted along a path. Alternatively, UV radiation (300 to 400 nm), in particular with a wavelength of approximately 355 nm and a pulse duration of between 0.1 and 10 ns, can be used.

The treatment apparatus 1 generates a cut in the material, the shape of which cut depends on the pattern with which the laser-pulse foci are/become arranged in the tissue. The pattern in turn depends on the path along which the focus is shifted. The path predetermines target points for the focus position to which one or more laser pulse(s) is (are) emitted and ultimately defines the shape and position of the cut.

Figure 3:
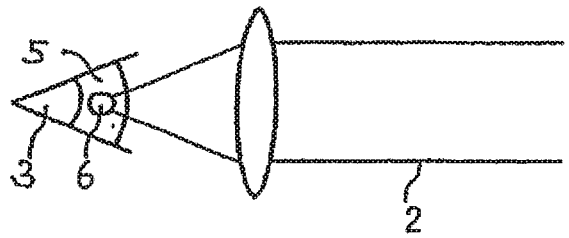
FIG. 3 depicts a basic principle for introducing pulsed laser radiation into the eye with the treatment apparatus of FIG. 1.

A possible effect of the laser beam 2 is indicated schematically in FIG. 3. It is focused into the material, e.g., the cornea 5 or lens of the eye by means of optics of the laser device L, not identified in more detail. As a result, a focus 6 forms in the material in which focus the energy density of the laser radiation is so high that, in combination with the pulse length, a non-linear effect occurs. For example, each pulse of the pulsed laser radiation 2 can produce at the respective spot of the focus 6 an optical break-through in the material, e.g., in the cornea 5 or lens, which is indicated schematically in FIG. 3 by way of example by a plasma bubble. As a result, material, e.g., tissue, is cut by this laser pulse. When a plasma bubble forms, the tissue layer is disrupted in a zone larger than the spot covered by the focus 6 of the laser radiation 2, although the conditions for producing the break-through are achieved only in the focus. In order for an optical break-through to be produced by every laser pulse, the energy density, i.e., the fluence, of the laser radiation must be above a certain threshold value which is dependent on wavelength and pulse length. This relationship is known to a person skilled in the art, for example, from DE 695 00 997 T2.

Alternatively, a material-cutting effect can also be produced through the pulsed laser radiation by emitting several laser radiation pulses in the one area, wherein the spots 6, i.e., sites of the focus 6, overlap for several laser radiation pulses. Several laser radiation pulses then interact to achieve a tissue-cutting effect, without plasma bubbles forming (so-called subthreshold regime). For example, the treatment apparatus 1 can use the principle which is described in WO 2004/032810 A2.

Figure 4:
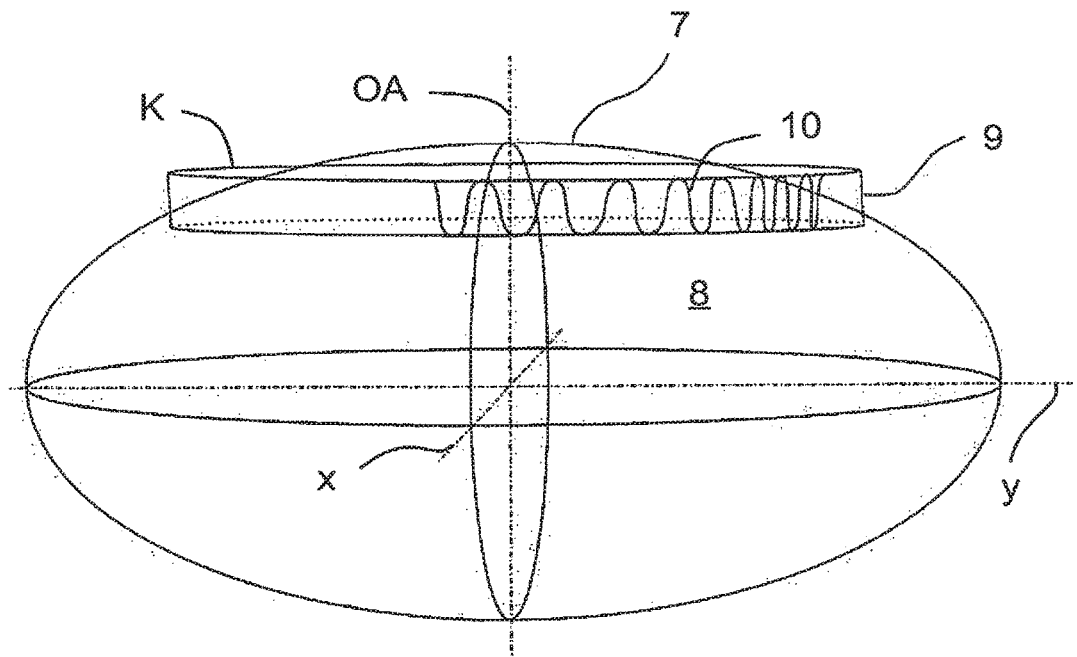
FIG. 4 depicts a schematic representation of a cut through a capsular bag of an eye.
Figure 5:
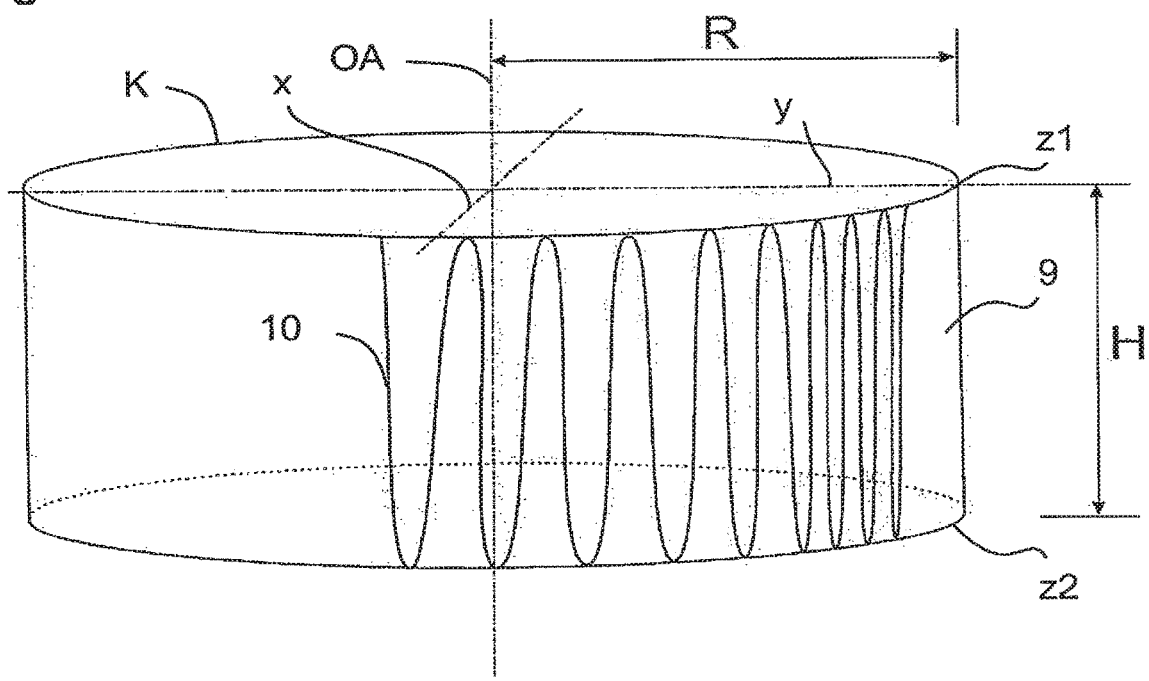
FIG. 5 depicts a schematic representation of the cut represented in FIG. 4.

By way of example, FIG. 4 shows the production of a cut 9 in a capsular bag which envelops a lens 8 of the eye 3. The cut 9 is bi-connected. It has the shape of a circular cylinder jacket, thus the lateral area of a cylinder, the generatrix of which is a circular curve K; however, other closed figures are also possible as generatrix of the cylinder, in particular any periodic Lissajous figure, including a crossing one.

The curve K defines the lateral shift of the focus, i.e., in the x/y-plane. The corresponding x/y-coordinates lie in the plane of the image field B of the laser device L. They are plotted in the figures by way of example. The position of the focus 6 is moved along the curve K perpendicular to the optical axis OA, which is the main direction of incidence of the optical laser radiation 2. Simultaneously the axial position of the focus oscillates along the optical axis OA, i.e., perpendicular to the x/y-plane. A path 10, which oscillates back and forth between an upper axial focus position z1 and a lower axial focus position z2, thereby generates the cut 9. These oscillations are carried out several times during the movement along the curve K.

This procedure avoids rapid lateral deflection of the laser radiation 2 over the zone to be treated, which is characterized in the described case by the radius R of the curve K and has a maximum lateral dimension of 2*K. Optionally, a size of the image field B is much smaller than this lateral extent. Generally, a rapid axial movement is carried out, while the lateral movement follows the curve K in the x/y-plane. A cut is thus produced which is substantially parallel to the optical axis. A simple optical system can thus be used which does not require a rapid but long-stroke lateral shift of the focus.

Several approaches come into consideration for the axial focus shift, for example, an electro-optical lens or a so-called two-stage z-scanner, which combines a slow, long-stroke shift with a rapid, short-stroke shift. The two stages of such a two-stage z-scanner can be formed spatially separated or combined.

For the case of treatment of the human lens, which is to be dealt with by way of example in the following, a maximum value NA=0.2 cannot be substantially exceeded for anatomical reasons. From this the effective focal length of the objective lens used results at least approximately at:

$$f \approx \frac{n \cdot D}{2 \cdot NA} \approx \frac{1.3 \cdot 6 \text{ mm}}{2 \cdot 0.2} \approx 19 \text{ mm}.$$

In order to travel the path 10, the axial shift must follow a path according to:

$$\zeta(t) = \zeta_{max} \sin(\overline{\omega} \cdot t).$$

For the acceleration the following is obtained corresponding by:

$$\ddot{\zeta}(t) = -\overline{\omega}^2 \cdot \zeta_{max} \sin(\overline{\omega} \cdot t)$$

The typical radius R for the curve K is between 2 and 3 mm in cataract surgery. The circumference of the cut is therefore approximately 20 mm. In order to achieve good material cutting in a technique based on plasma bubbles, the tangential path dimension (adjacent axial oscillations) should be between 1 and 10 µm. Approximately between 2,000 and 20,000 vertical cut path sections are thus to be produced. The spacing between the spots should be in the order of between 1 and 10 µm on each cut path section.

The height H must correspond at least to the thickness of the capsular bag, thus approximately to 20 to 25 µm. If it is smaller, several cuts 9 can be "stacked" on top of each other in order to sever the capsular bag, wherein a certain overlap can be useful.

A total height of from 25 µm to 250 µm seems to be practical. The cut 9 thus has a unit area of from approximately 500,000 to 5,000,000 µm². 50,000 to 5,000,000 laser spots are thus positioned with a grid constant of from 1×1 µm to a maximum of 10×10 µm.

At a laser pulse repetition rate of 100 kHz, a minimum cut production time (without breaks or down times) of from 0.5 to 50 s results. Since pulse energies in the µJ range can be easily produced at such a laser pulse repetition rate it is preferred to combine a larger average spot distance with higher energy, e.g., 0.5 µJ and 3×3 µm. The production time for the cut is thus only a few seconds (less than 10 s) even in the case of tall cylinders.

Alternatively, with low pulse energy (<100 nJ) and a laser pulse repetition rate in the range of a few MHz a spot distance of 1×1 µm can be used. For example, at 5 MHz a production time for the cut of only a few seconds (less than 10 s) likewise is obtained again.

This means that the axial adjustment must realize 2,000 to 20,000 axial oscillations within approximately 5 seconds during the lateral circuit around the curve K having a circumference of 20 mm depending on the path distance. The axial frequency (oscillation frequency) is thus 500 Hz to 5 kHz. For the acceleration the following results:

$$\text{Max}(\ddot{\zeta}(t)) = \overline{\omega}^2 \cdot \zeta_{max} = 4\pi^2 f^2 \cdot \zeta_{max} \approx 10^{6 \cdots 11} s^{-2} \cdot \zeta_{max}.$$

Figure 6:
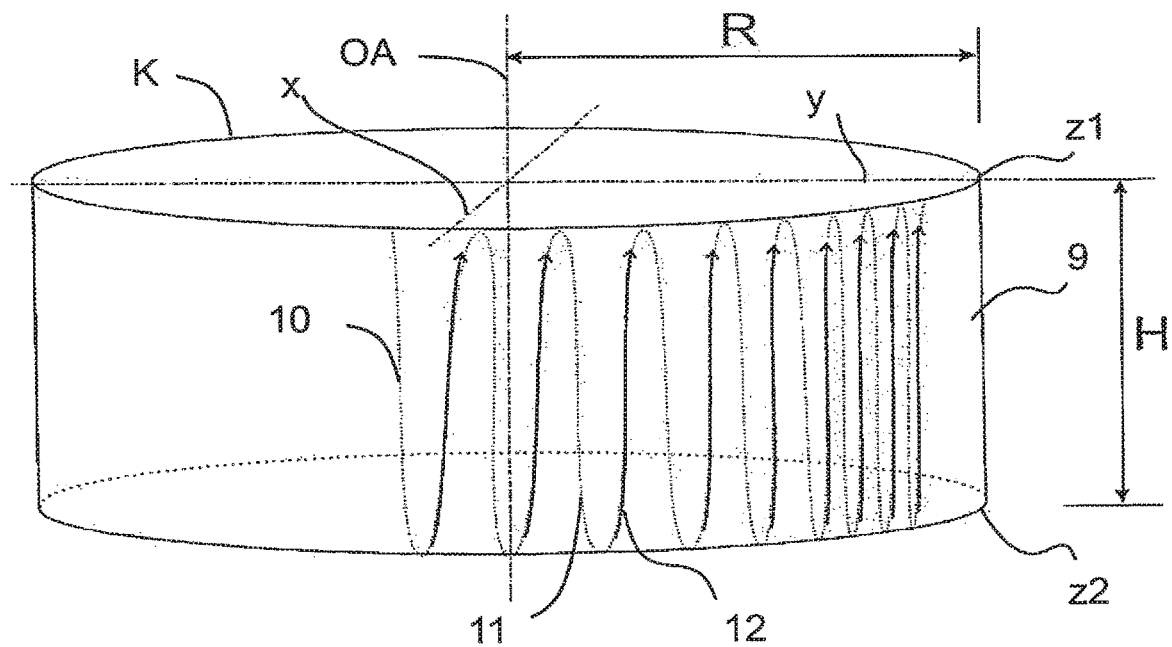
FIG. 6 depicts a schematic representation similar to FIG. 5 to illustrate the guiding of the laser beam on a path.

It is to be borne in mind that the type of the path 10 does not automatically prevent unfavorable influencing of the optical beam path through the material (tissue) by previous interactions, as would be the case in the layer-by-layer construction of the cut along the direction of incidence of the laser radiation. Therefore, according to FIG. 6, a refinement is provided, by modifying the laser radiation 2 on sections 11 of the path 10 into the depth of the material (away from the direction of incidence) such that no interaction occurs which might interfere with the transmission of subsequent pulses, or this is at least reduced. In the simplest case, the pulses are completely suppressed on these sections 11. This concept can also be extended to the areas near the reversal points of the path, thus up to approximately 40% in the vicinity of the turning points of the path 10 (not necessarily symmetrically).

Figure 7:
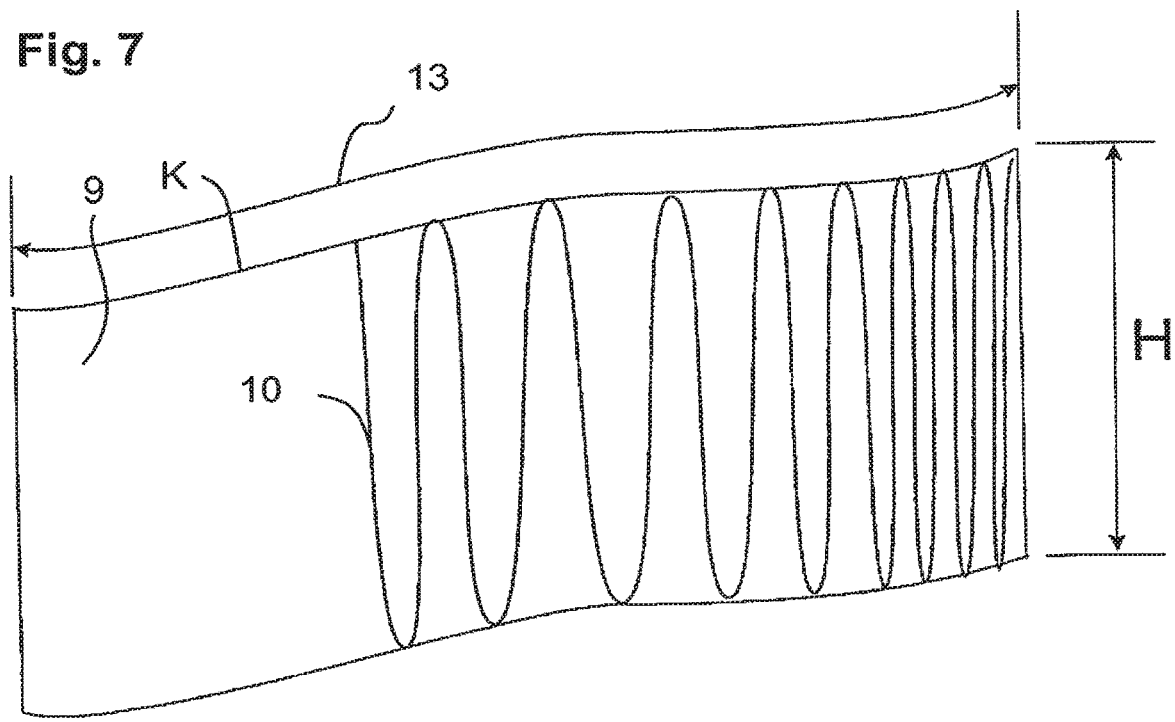
FIG. 7 depicts a schematic representation of a cut which, unlike the cut in FIG. 4, does not surround a zone.

FIG. 7 shows by way of example a cut 9, which is simply connected in the mathematical sense, the curve K of which is thus not closed to form a loop. The maximum dimension of the cut 9 thus results from the length 13 of the curve K. The focus is, in turn, shifted lateral along the curve K. While travelling the length 13 the focus is at the same time shifted axial in an oscillating manner.

The absolute position of the axial upper and lower focus position varies along the curve K. This is, of course, not compulsory; constant axial upper and lower focus positions can also be used, too. There is just as little need for the distance between the axial upper and lower focus position, between which the oscillation is carried out, to be constant. As a result, the position of the focus follows the meandering path 10 in the cut 9, and the axial upper and lower focus position(s) of the oscillation predetermine(s) the upper and lower edge of the cut 9 respectively. This is equally possible for bi-connected cuts.

Figure 8:
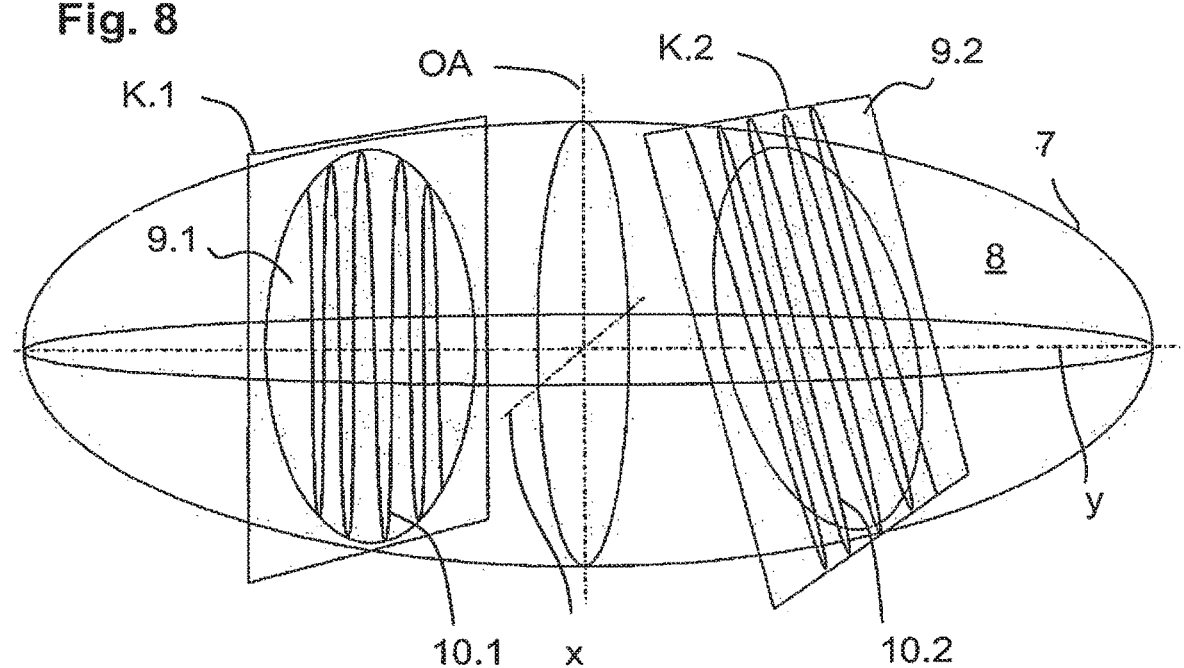
FIG. 8 depicts a schematic representation similar to FIG. 4 illustrating a possible application of the cut of FIG. 7.

FIG. 8 shows by way of example possible applications for such cuts. In each case two cuts are represented in turn on a capsular bag, enveloping a crystalline lens. Two cuts 9.1 and 9.2 which have curves K.1 and K.2 are shown by way of example.

The left-hand cut 9.1 is an example wherein the upper and lower focus position can vary during the movement along the curve K.1. The oscillation along the trajectory 10.1 is thus synchronized with the position along the curve K.1, with the result that e.g., the cut is produced in the shape of a circular disc shown in FIG. 8. It is thus possible, as shown in the embodiment of FIG. 8, to restrict the cut to a desired section of the transparent material, to the crystalline lens here, without impairing other material structures, the capsular bag here.

The right-hand cut 9.2 illustrates that the cut can also deviate from being strictly parallel to the optical axis OA. As in the left-hand cut 9.1, the axial focus shift here is also synchronized with the lateral focus shift. Now, however, the effect is that an additional lateral focus shift synchronized to the axial focus shift is carried out in order to incline the cut 9.2 slightly against the optical axis OA. Of course, this inclination can also be restricted to sections of the cut 9.2. This additional lateral focus shift is to be achieved particularly simply in the treatment apparatus of FIG. 2 when the focus is shifted additionally in a suitable manner within the image field B. The cut 9.2 is still substantially parallel to the optical axis OA, since the additional lateral focus shift in synchronization with the axial focus shift is small compared with the extent of the curve K.

The axial focus shift can be carried out simply if the amplitude can be minimized. This is preferably the case when a z-scanner is configured such that the optical scale ratio of focus movement to z-scanner movement is less than 1:2, preferably even less than 1:1. This means that the mechanical path variation in the scanner is not greater than the focus movement in the object. The acceleration is then in the range of from 0.1 to $10^3$ m/s².

An optional means for achieving such a value is a reflective z-scanner, the optical design of which is provided to avoid a beam focus in a conventional scan path being positioned on an optical boundary surface of the scanner.

A further optional means consists of the z-scanner having, as a drive, a piezo stack or a plunger coil which is operated as resonantly as possible. It is also an option to bring about the reflection by means of an electro-optical component (e.g., AOM).

As mentioned, a second z-scanner can also be used, which realizes additional divergence changes (positive or negative) of the laser beam that are slow over time, wherein the scanner is controlled by a control unit, which takes into account the position signals (measurement signal) or control signals of one scanner during the control of the respectively other scanner, because, for example, both control signals are produced in the control unit. The control unit can be realized by the control device 6.

Figure 9:
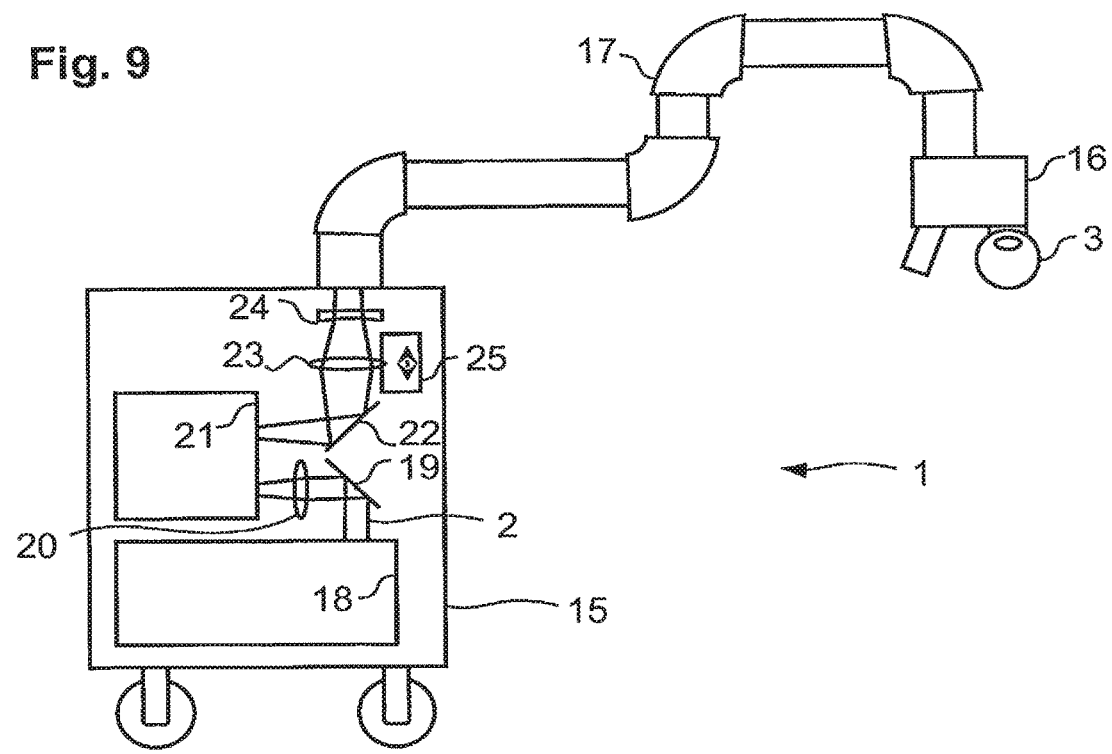
FIG. 9 depicts a schematic representation of a treatment apparatus that is designed for cataract surgery.

The treatment apparatus 1 represented schematically in FIG. 9 provides a rapid variation of the focus position along the optical axis, i.e., a rapid z-scanner, for the field of ophthalmological surgery, in particular for cataract surgery. In this treatment apparatus 1, elements which have already been explained with reference to the previous figures and which have the same function or structure in the treatment apparatus 1 are provided with the same reference numbers and are therefore not necessarily explained again.

The treatment apparatus 1 has a base part 15, which provides the laser radiation 2 and a handpiece 16, to which the laser radiation is transmitted. The transmission takes place by means of an articulated arm 17, which preferably has free space optics, which can be realized, for example, by suitable deflecting mirrors (not shown). It is disadvantageous to use optical fibers, as there are problems related to the radiation intensities of the laser radiation 2 required. However, optical fibers can be used in or instead of the articulated arm 17.

Figure 10:
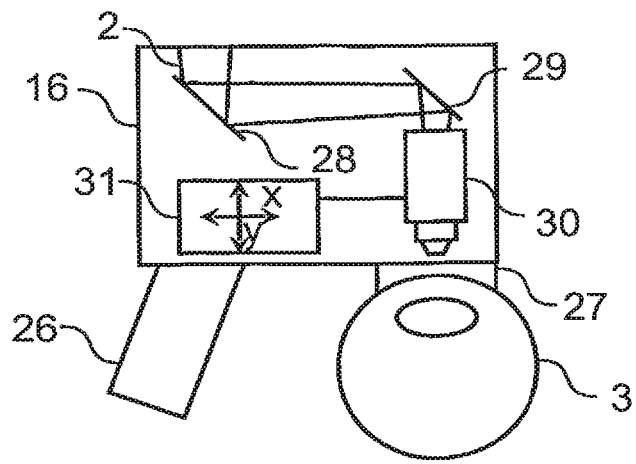
FIG. 10 depicts a schematic representation of a handle of the treatment apparatus of FIG. 9.

The handle 16 is placed on the eye 3. It is shown in detail in FIG. 10 and explained below.

The z-scanner and xy-scanner are realized in the base part 15 and in the handpiece 16. Both elements thus form, together with the articulated arm 17, the laser device L. The z-scanner is provided in the base part 15 in the structure of FIG. 9. A laser source 18 emits the laser radiation 2, which is transmitted via a deflecting mirror 19 and a lens 20 into a non-collimated beam path in the z-scanner 21, the structure of which will be explained below with reference to FIGS. 11, 13 and 14. The z-scanner outputs, the laser radiation 2 to the articulated arm 17 via a deflecting mirror 22 and lenses 23, 24 as a non-collimated beam. The lenses 23, 24 form a telescope, which can be adjusted via a drive 25. The significance of this telescope will be explained below.

When configured as bulk optics, the articulated arm 17 contains a series of deflecting mirrors and optionally a relay optical unit, in order to transmit the non-collimated beam to the output side of the articulated arm.

The handpiece 16 receives the laser radiation 2 as a non-collimated beam from the articulated arm 17 and outputs it into the eye 3 via a contact lens 27. A grip 26 is provided for positioning the handpiece 16.

The laser radiation 2 is guided in the handpiece 16 via deflecting mirrors 28 and 29 to an objective lens 30, which is displaced by an actuator 31 transverse to the optical axis. This realizes the already-mentioned image field shift. The objective lens 30 is not a field objective lens, i.e., not an objective lens which is telecentric on the image side, but, the laser radiation is focussed into different depths in the eye 3 depending on the divergence or convergence of the beam at the entrance pupil of the objective lens 30. Thus the variation in the propagation of the beam brought about by the z-scanner is converted into a variation in the axial focus position in the eye 3.

To adjust the image field, the objective lens 3 is moved laterally in the handpiece 16 by the actuator 31. At the same time, the deflecting mirrors 28 and 29 in the handpiece 16 are mechanically controlled and repositioned by the control device C for the displacement of the objective lens 30 such that the laser radiation 2 always remains a centered beam in the entrance pupil of the objective lens.

Figure 11:
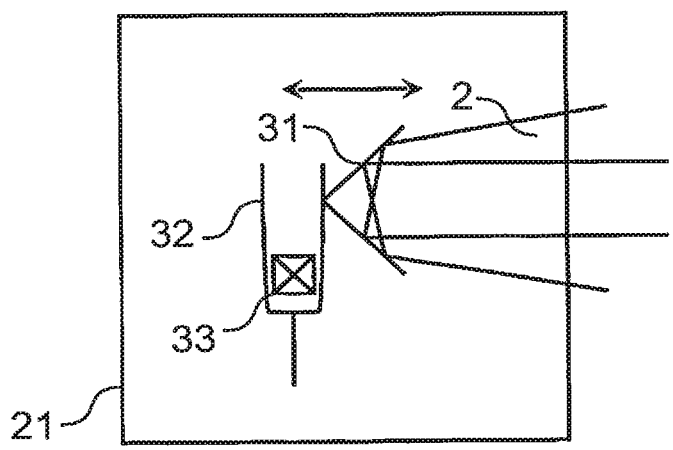
FIG. 11 depicts a schematic representation of a z-scanner of the treatment apparatus of FIG. 9.

FIG. 11 shows the effect of the z-scanner 21 schematically. It has a corner mirror 31, which realizes a retroreflector. In principle, the corner mirror 31 can be replaced by any different type of retroreflector. The corner mirror 31 is fixed to a tuning fork 32, which is made to vibrate by an exciter 33. The corner mirror is illuminated by the non-collimated beam of the laser radiation 2. By adjusting the position of the corner mirror, the length of the non-collimated beam path is changed, and thus the propagation of the diverging beam of the laser radiation 2.

Figure 13:
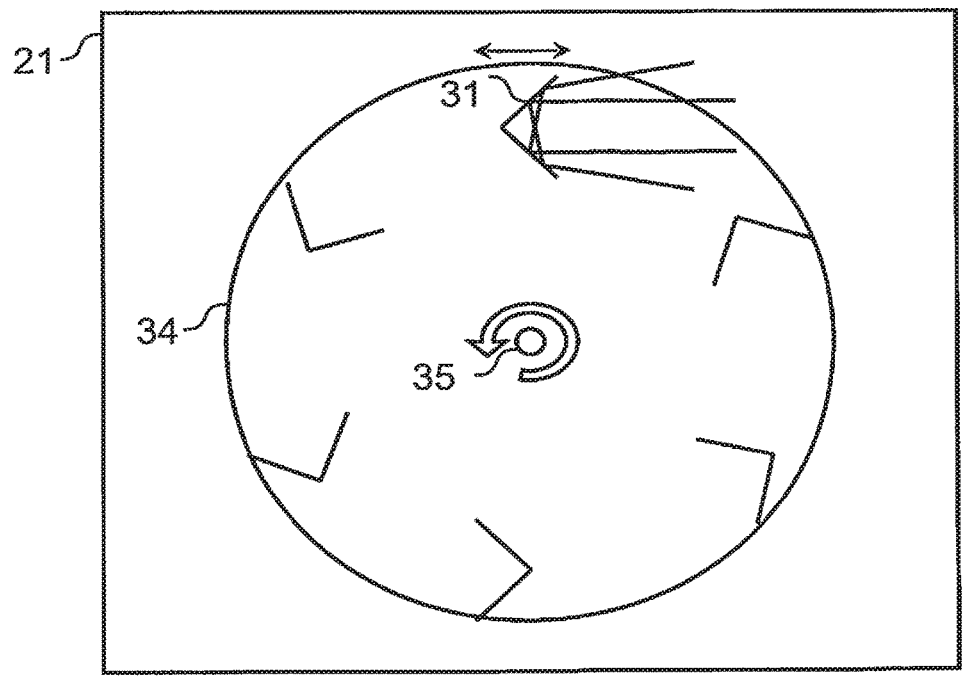
Figure 14:
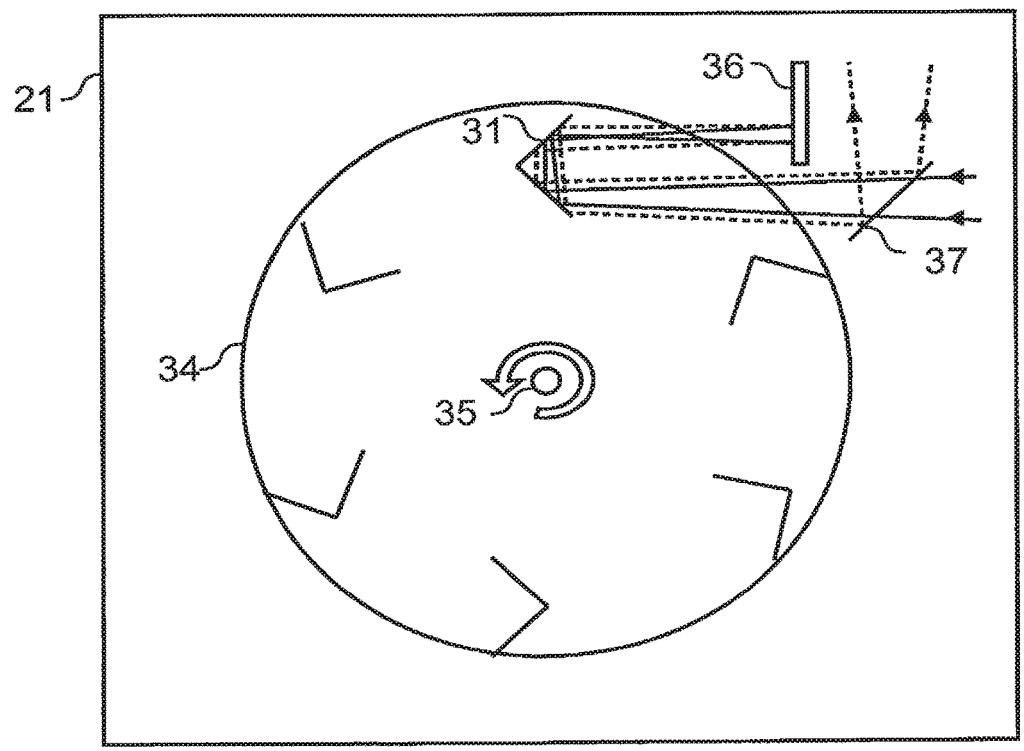

FIGS. 13 and 14 show alternatives for the scanner 21. According to FIG. 13, a large number of corner mirrors 31 are fixed on a rotating disc 34, which is made to rotate about an axis 35. The rotation has the effect that the optical path length of the diverging beam section is adjusted. The advantage is a more rapid adjustment, the disadvantage is a lower repeat accuracy and an increased outlay on adjustment for the several corner mirrors 31. FIG. 14 shows another refinement, which in addition to the structure of FIG. 13 also has an end mirror 36 and a beam splitter 35. The incident, diverging beam of the laser radiation 2 passes through the beam splitter 37, is deflected at the corner mirror 31 to the end mirror 36, reflected there (from now on the beam path is shown by a dashed line), reflected again by the corner mirror 31 and then coupled out by the beam splitter 37. The path length adjustment which occurs during the rotation of the disc 34 is thus twice as large, with the result that a higher adjustment speed is achieved at the same rotation speed of the disc 34.

In order to generate targeted cuts in the eye according to the above-described cut methodology, the actuator 31 move the objective lens 31 laterally in the handpiece 16 (by repositioning the deflecting mirrors 28 and 29). During this lateral movement, the telescope 23, 24 is readjusted synchronously by the drive 25. This is necessary because the optical path length from the scanner 21 to the objective lens 30 varies due to the lateral movement of the objective lens 31. Since the beam of the laser radiation 2 is non-collimated when it strikes the objective lens 30, the change in path length would additionally lead to a change in the z position of the focus. The desired z-scanner property would thus be disrupted. The divergence/convergence of the light beam is therefore adjusted synchronously with the movement of the objective lens 30 with the aid of the telescope 23, 24.

Figure 12:
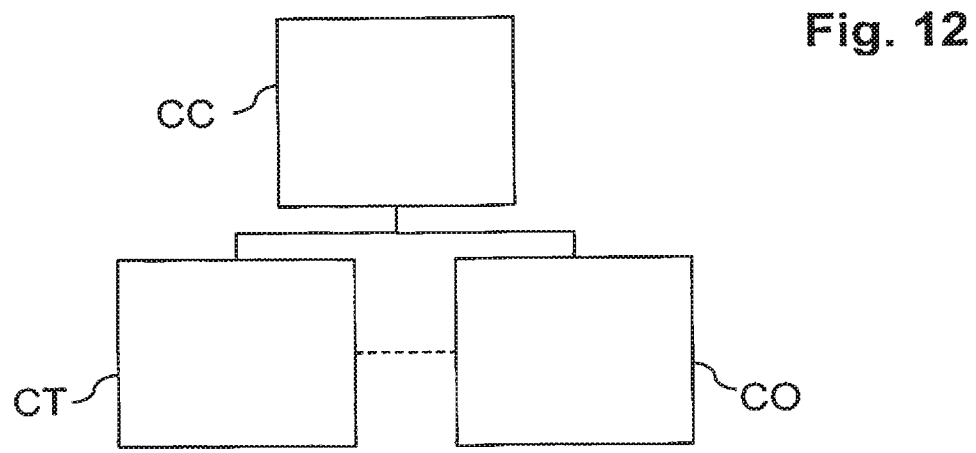
FIG. 12 depicts a schematic block diagram for the control concept of the treatment apparatus of FIG. 9, and FIGS. 13 and 14 depict schematic representations for alternative embodiments of the z-scanner of the treatment apparatus of FIG. 9.

FIG. 12 shows a block diagram of a control set-up provided for this purpose. Here the control device C is shown in the form of three functions. A central control block CC controls two sub-blocks, a control block CT to control the telescope 23, 24 and a control block CO for the actuator 31, i.e., to displace the objective lens 30. The synchronized control of the shift of the transverse position of the objective lens 30 and of the shift of the telescope 23, 24 has the result that the position of the focus in the depth direction is exclusively set by the z-scanner 21, and that the shift of the image field B does not bring with it a simultaneous displacement of the depth position of the focus. In other words, the synchronous shift of the telescope 23, 24 being a means of influencing the divergence/convergence of the radiation striking the objective lens 30 and the transverse shift of the objective lens ensure that the image field is moved in a plane perpendicular to the optical axis and not on a curved trajectory.

When treating cataracts it is advantageous to provide navigation properties which make it possible to determine the position of the structures to be treated, for example, the position of the capsular bag or the lens. In a system with a mechanically-movable optical unit for the lateral focus shift, which has an image field which is smaller than the structure to be found or the cut to be produced, different variants come into consideration.

Variant 1—Confocal detection: For measuring the topography of the eye 3 in the area of the cornea 5 and/or the lens 8, back-reflected light is deflected with the aid of polarization optical units, focused on a diaphragm and recorded using a photodetector. The wavelength of the laser radiation 2 is used for this measurement. Using the z-scanner confocal signals from a small scanning range of 10-100 μm are sensed. The signals recorded by the photodetector are amplified e.g., with a lock-in method or boxcar integrator. The reference frequency for the lock-in amplifier equals the scanning frequency of the rapid z-scanner. The confocal signals are recorded during the (slow) movement of the objective lens. The image field B moves along the curve K, which matches the pattern for the laser treatment. At the same time, the axial focus position is adjusted, with the result that a path (e.g., the path 10) is traveled. In this way, the exact position is determined where laser desorption is to take place and thus the safety of the treatment is increased.

Variant 2—OCT detection: In this variant, the topography of the eye 3 in the area of the cornea 5 and/or the lens 8 is measured using short-coherent light, which has a different wavelength. The light from a short-coherent source is coupled into the optical unit O using a dichroic mirror. The light reflected back by eye structures is deflected by the same dichroic mirror and detected using an interferometric arrangement. In order to make the laser treatment safe and precise, an objective lens is used which has a numerical aperture in the range 0.15-0.2. In a fully-illuminated entrance pupil of the objective lens, the z-axial measurement range of the OCT detection is limited by the depth of field of the objective lens. Accordingly, here the short-coherent illumination is designed (e.g., by corresponding selection of the collimator geometry or using a diaphragm) such that only part of the entrance pupil of the objective lens O is illuminated. Since the effective numerical aperture of the focused short-coherent light is thereby reduced, a larger depth range is realized here for the OCT detection.

Preferably, in these navigation measurements, no tomographic image acquisition of the eye structures occurs, but is simulated and matched to a computational eye model using depth-resolved measurements at selected points the eye structure. The result of this matching is represented as an optional animation. Using this animation, the surgeon is in a position to set the spatial boundaries of the photodesorption.

In an embodiment, the depth-resolved navigation measurements take place along the path which is used for the laser treatment. If these measurements reveal a decentering of the circular pattern of the planned capsular bag opening in relation to the crystalline lens, optionally, a new series of navigation measurements is taken. The data obtained in this way are correlated again with the computational eye model and the result is displayed as an animation for checking the laser treatment.

The invention claimed is:

1. A method for producing a cut surface in a transparent material of an eye, the method comprising:
    providing optical radiation;
    focusing the optical radiation along an optical axis into a focus situated in the transparent material and providing an image field in which the focus lies and which has an image field size;
    defining the cut surface and a path located in the cut surface along which path a position of the focus is to be shifted, wherein the cut surface extends substantially parallel to the optical axis and, in projection along the optical axis, comprises a curve which has a maximum extent along the optical axis,
    wherein the path prescribes moving the position of the focus along the optical axis in multiple oscillations between an upper axial focus position and a lower axial focus position and prescribes moving the position of the focus transverse to the optical axis along the curve,
    wherein the cut surface, transverse to the optical axis, has a maximum extent which is greater than the image field size and
    generating the cut surface in the transparent material by moving the position of the focus along the path, wherein moving the position of the focus along the path further comprises shifting the image field transverse to the optical axis to move the position of the focus transverse to the optical axis.

2. The method according to claim 1, further comprising deactivating the optical radiation, while the focus is on sections of the path in which the position of the focus moves with a direction of incidence of the optical radiation, wherein deactivating the optical radiation comprises either to switch off or to modifies the optical radiation such that the optical radiation has no material-cutting effect in the transparent material.

3. The method according to claim 1, wherein the oscillations are asymmetrical with sections of the path in which the position of the focus moves with the direction of incidence of the optical radiation run more steeply than other sections of the path in which the position of the focus moves contrary to the direction of incidence of the optical radiation.

4. The method according to claim 1, wherein the cut surface has a shape of a cylinder jacket.

5. The method according to claim 1, wherein the upper axial focus position defines an upper edge of the cut surface and the lower axial focus position defines a lower edge of the cut surface.

6. The method according to claim 1, wherein shifting the image field transverse to the optical axis comprise to move optics transverse to the optical axis.

7. The method according to claim 1, wherein the curve is a periodic Lissajous figure.

8. The method according to claim 1, wherein the curve is a closed curve.

9. The method according to claim 1, wherein moving the focus along the optical axis in multiple oscillations is synchronized with shifting the image field transverse to the optical axis.

10. The method according to claim 1, wherein the optical radiation is pulsed optical radiation and wherein one or several pulses near turning points of the multiple oscillations are suppressed or deactivated regarding material-cutting effect in the transparent material.

11. A treatment apparatus for producing a cut surface in a transparent material of an eye, which apparatus comprises a laser source configured to provide optical radiation which is adapted to separate the transparent material;

optics configured to focus the optical radiation along an optical axis into a focus situated in the transparent material and which have in the transparent material an image field in which the focus lies and which have an image field size;

a focus adjustment device for adjusting a position of the focus transverse to the optical axis and along the optical axis, wherein the focus adjustment device is configured to move the position of the focus transverse to the optical axis by a shift of the image field transverse to the optical axis, and a control device which is connected to the laser device and is configured to define the cut surface and a path located in the cut surface along which path the position of the focus is to be shifted so as to generate the cut surface in the transparent material along the path, wherein the control device is configured to control the laser device such that the cut surface extends substantially parallel to the optical axis and, in projection along the optical axis, and comprises a curve which has a maximum extent along the optical axis, wherein, during movement of the focus along the curve, the control device defines the position of the focus by a multiple oscillating adjustment of the position of the focus along the optical axis between an upper axial focus position and a lower axial focus position, and wherein the control device is configured to control the laser device such that the cut surface, transverse to the optical axis, has a maximum extent which is greater than the image field size and that the focus adjustment device defines a movement of the position of the focus transverse to the optical axis along the curve.

12. The apparatus according to claim 11, wherein the control device switches off or modifies the optical radiation such that the optical radiation has no material-cutting effect in the transparent material while the focus is on sections of the path in which the position of the focus moves with a direction of incidence of the optical radiation.

13. The apparatus according to claim 12, wherein the oscillations are asymmetrical with sections of the path in which the position of the focus moves with the direction of incidence of the optical radiation running more steeply than other sections of the path in which the position of the focus moves contrary to the direction of incidence of the optical radiation.

14. The apparatus according to claim 11, further comprising a base part, a movable distal part and a flexible or articulated, optical transmission device, which connects the base part to the distal part, wherein the base part couples the radiation into the transmission device as a non-collimated beam, the transmission device transmits the non-collimated beam to the distal part, the distal part comprises an objective lens, which receives the non-collimated beam and focuses it into the eye, and the focus adjustment device for moving the position of the focus is formed by two parts and comprises a first scanner, which moves the position of the focus along the optical axis and is arranged in the base part, and a second scanner, which moves the position of the focus transverse to the optical axis, wherein the second scanner comprises an actuator for displacing the objective lens transverse to the optical axis and a divergence-adjusting device, which changes a divergence or convergence of the non-collimated beam, and wherein furthermore the control device is designed such that it controls the divergence-adjusting device to act synchronously with the actuator for displacing the objective lens.

15. The apparatus according to claim 14, wherein the divergence-adjusting device is arranged in the base part or comprises a telescope and an actuator that adjusts the telescope.

16. The apparatus according to claim 14, wherein the first scanner changes a path length of the non-collimated beam, through the use of at least one displaceable corner mirror to move the position of the focus along the optical axis.

17. The apparatus according to claim 16, wherein the first scanner comprises an oscillator for periodically changing the path length or the first scanner comprises several corner mirrors, which are mounted on a rotating disc.

18. The apparatus according to claim 14, wherein the distal part comprises a repositioning device which holds the non-collimated beam centred in a pupil of the objective lens synchronously with the displacement of the objective lens.

19. The apparatus according to claim 11, wherein the cut surface has a shape of a cylinder jacket.

20. The apparatus according to claim 11, wherein the optical radiation is pulsed optical radiation and the control device suppresses or deactivates one or several pulses near turning points of the multiple oscillations regarding a material-cutting effect in the transparent material.

21. A method for producing a cut surface in a transparent material of an eye, the method comprising:

providing optical radiation;

focusing the optical radiation along an optical axis into a focus situated in the transparent material and providing an image field in which the focus lies and which has an image field size;

defining the cut surface and a path located in the cut surface along which path a position of the focus is to be shifted, wherein the cut surface extends substantially parallel to the optical axis and, in projection along the optical axis, comprises a curve which has a maximum extent along the optical axis, wherein the path prescribes moving the position of the focus along the optical axis in multiple oscillations between an upper axial focus position and a lower axial focus position and prescribes moving the position of the focus transverse to the optical axis along the curve, wherein the cut surface, transverse to the optical axis, has a maximum extent which is greater than the image field size and generating the cut surface in the transparent material by moving the position of the focus along the path, wherein moving the position of the focus along the path further comprises shifting the image field transverse to the optical axis to move the position of the focus transverse to the optical axis, and wherein the optical radiation is pulsed optical radiation and wherein one or several pulses of the pulsed optical radiation are suppressed or deactivated regarding a material-cutting effect of the transparent material near turning points of the multiple oscillations.

* * * * *